United States Patent
Zhu et al.

(10) Patent No.: US 12,129,278 B2
(45) Date of Patent: Oct. 29, 2024

(54) HIGH-AFFINITY PEPTIDE FOR TUMOR NECROSIS FACTOR ALPHA AND APPLICATION THEREOF

(71) Applicant: Naishuo Zhu, Shanghai (CN)

(72) Inventors: Naishuo Zhu, Shanghai (CN); Changwu Hu, Shanghai (CN)

(73) Assignee: Naishuo Zhu, Shanghai (CN)

( * ) Notice: Subject to any disclaimer, the term of this patent is extended or adjusted under 35 U.S.C. 154(b) by 1509 days.

(21) Appl. No.: 16/477,488

(22) PCT Filed: Jan. 11, 2018

(86) PCT No.: PCT/CN2018/072194
§ 371 (c)(1),
(2) Date: Jul. 11, 2019

(87) PCT Pub. No.: WO2018/130170
PCT Pub. Date: Jul. 19, 2018

(65) Prior Publication Data
US 2023/0192768 A1    Jun. 22, 2023

(30) Foreign Application Priority Data

Jan. 12, 2017 (CN) .......................... 201710019149.8

(51) Int. Cl.
| | |
|---|---|
| *C07K 7/08* | (2006.01) |
| *A61K 38/00* | (2006.01) |
| *C07K 14/00* | (2006.01) |
| *G01N 33/532* | (2006.01) |
| *G01N 33/68* | (2006.01) |

(52) U.S. Cl.
CPC .............. *C07K 14/001* (2013.01); *C07K 7/08* (2013.01); *G01N 33/532* (2013.01); *G01N 33/6863* (2013.01); *A61K 38/00* (2013.01); *G01N 2333/525* (2013.01)

(58) Field of Classification Search
None
See application file for complete search history.

(56) References Cited

U.S. PATENT DOCUMENTS

2017/0101442 A1*  4/2017  Cheng .................... C07K 14/00

OTHER PUBLICATIONS

Liu, S., "Panning and identification of antagonistic active peptides specifically bin-ding to the first and second extracellular membrane loops of rat CCR5 by technique of phage display peptide library / 中国病理生理杂志" Chinese Journal of Pathophysiology, Abstract (Year: 2015).*
Diaz-Perlas, C., et al., "Phage display as a tool to discover blood-brain barrier (BBB)-shuttle peptides: panning against a human BBB cellular model", Peptide Science, pp. 1-13 (Year: 2016).*
You, F., et al., "Biopanning and characterization of peptides with Fe3O4 nanoparticles-binding capability via phage display random peptide library technique", Colloids Surf B Biointerfaces, pp. 537-545 (Year: 2016).*

* cited by examiner

*Primary Examiner* — Jennifer Chin
(74) *Attorney, Agent, or Firm* — Flener IP & Business Law; Zareefa B. Flener

(57) ABSTRACT

Peptide with high binding affinity for tumor necrosis factor alpha (TNF-α). The peptide has an amino acid sequence of SEQ.ID.NO.1, or the peptide is a tandem or branched peptide with a single repeat or multiple repeats of SEQ.ID.NO.1 and SEQ.ID.NO.3 and has an amino acid sequence of SEQ.ID.NO.4. The peptide can bind to TNF-α with high affinity and can antagonize TNF-α function. When being directly injected to an animal, the peptide can significantly reduce the degree of inflammation of an animal body and improve the resistance of the animal body on an inflammatory damage. The peptide can be used for developing TNF-α antagonist drugs for treating various acute and chronic inflammatory damage, such as inflammatory, auto-immune and stress damage caused by physical, chemical and biological factors. Thus, the peptide has an extremely wide application prospect. Moreover, the peptide has a small molecular weight and low immunogenicity, and is easy to synthesize, thereby avoiding the side effects and disadvantages of traditional monoclonal antibody drug antagonists.

4 Claims, 2 Drawing Sheets
Specification includes a Sequence Listing.

SEQUENCE LISTING

```
<160> NUMBER OF SEQ ID NOS: 4

<210> SEQ ID NO 1
<211> LENGTH: 7
<212> TYPE: PRT
<213> ORGANISM: Artificial Sequence
<220> FEATURE:
<223> OTHER INFORMATION: synthesized

<400> SEQUENCE: 1

His Tyr Ile Asp Phe Arg Trp
1               5

<210> SEQ ID NO 2
<211> LENGTH: 21
<212> TYPE: DNA
<213> ORGANISM: Artificial Sequence
<220> FEATURE:
<223> OTHER INFORMATION: synthesized

<400> SEQUENCE: 2
cattatattg attttaggtg g                                                 21

<210> SEQ ID NO 3
<211> LENGTH: 12
<212> TYPE: PRT
<213> ORGANISM: Artificial Sequence
<220> FEATURE:
<223> OTHER INFORMATION: synthesized

<400> SEQUENCE: 3

Lys Ala Ser Gly Ser Pro Ser Gly Phe Trp Pro Ser
1               5                   10

<210> SEQ ID NO 4
<211> LENGTH: 21
<212> TYPE: PRT
<213> ORGANISM: Artificial Sequence
<220> FEATURE:
<223> OTHER INFORMATION: synthesized

<400> SEQUENCE: 4

His Tyr Ile Asp Phe Arg Trp Asp Met Lys Ala Ser Gly Ser Pro Ser
1               5                   10                  15

Gly Phe Trp Pro Ser
            20
```

HIGH-AFFINITY PEPTIDE FOR TUMOR NECROSIS FACTOR ALPHA AND APPLICATION THEREOF

TECHNICAL FIELD

The present invention belongs to the field of biotechnology. The invention specifically relates to a peptide with high affinity for tumor necrosis factor alpha (TNF-α), TNF-α antagonist peptide, and use thereof.

BACKGROUND ART

Tumor necrosis factor, which was originally induced by endotoxin injection in 1975, is identified as a serum active factor that induces apoptosis of tumors transplanted into mice and is therefore named as tumor necrosis factor. As research progressed, TNF-α was found to be a very important inflammatory factor. In immune-mediated inflammatory diseases, the expression of TNF-α in tissue is increased, inducing a series of pathogenic reactions and expression of related inflammatory factors, ultimately leading to the tissue damage (e.g., bone destruction, cartilage degradation, fibroblast proliferation, keratinocyte proliferation, etc.). Thus, TNF-α is an important target for the treatment of a variety of inflammatory diseases.

The existing TNF-α antagonists mainly focus on monoclonal antibodies and their derivatives. However, monoclonal antibody based drugs are highly immunogenic, and they can induce the production of anti-drug antibodies (i.e., anti-antibodies) in vivo, which undoubtedly affect the therapeutic efficacy of the drug. On the other hand, monoclonal antibody based drugs may induce antibody-dependent cell-mediated cytotoxicity (ADCC) and complement-dependent antibody-mediated cytotoxicity, which may cause damage and side effects to the body in addition to the decrease in efficacy caused by the production of anti-antibodies. Different molecular structures determine the immunogenicity of the molecule. Compared with antibody, peptide is less immunogenic, and more tissue-permeable due to its small molecular size. Therefore, peptide is a more advantageous TNF-α antagonist. It is convenient to observe whether a peptide has an inhibitory effect on inflammation by synthesizing a sequence-specific peptide, and detecting the affinity of the antagonist peptide to TNF-α using ELISA, followed by injecting the antagonist peptide into an animal with inflammation.

SUMMARY OF THE INVENTION

The object of the present invention is to provide a peptide with high binding affinity for tumor necrosis factor alpha and use of the peptide in antagonizing the function of tumor necrosis factor alpha.

The present disclosure provides a peptide with high affinity for TNF-α, wherein the peptide has an amino acid sequence as set forth in SEQ.ID.NO.1. The peptide is referred to as peptide 632 or TNF-α antagonist peptide. The peptide has the following functional characteristics: (1) a highly affinity for TNF-α, and a dissociation constant Kd of 138 nM (Kd value indicates the concentration of ligand when half of the receptor is bound by the ligand, and the smaller the Kd value, the higher the affinity of the receptor to the ligand); (2) it can effectively inhibit the onset of inflammation after being injected into an animal model of inflammation, thereby preventing inflammatory damage.

The present disclosure also provides a gene encoding the peptide with high affinity for TNF-α (consisting of degenerate codons of the corresponding amino acids), wherein the gene has a nucleotide sequence as set forth in SEQ.ID.NO.2.

The present disclosure also obtains a peptide having the same function as the peptide with high affinity for TNF-α by biotechnological modification, wherein the peptide has an amino acid sequence as set forth in SEQ.ID.NO.3 and is referred to as peptide 636.

The present disclosure also provides a peptide, comprising amino acid sequences of peptides with high affinity for TNF-α as set forth in SEQ.ID.NO.1 and SEQ.ID.NO.3, wherein the peptide is a single repeated or multiple repeated tandem or branched peptide molecular sequence, and a molecular comprising these core sequence features (i.e., having a homology of more than 70%), wherein the molecular has an amino acid sequence as set forth in SEQ.ID.NO.4.

The present disclosure also provides a peptide modified by a biological material or a chemical group, comprising SEQ.ID.NO.1 and SEQ.ID.NO.3 of peptides with high affinity for TNF-α as a core sequence, and being a structurally characteristic molecule linked with an antigen or a drug, or modified by PEG or covalently modified by other molecular groups on its C-terminal (or N-terminal, or side-chain) group.

The present disclosure also provides a modified peptide, comprising the above peptide with high affinity for TNF-α, wherein the modified peptide is labeled with a FITC fluorophore, an isotope, a chemiluminescent group or an enzyme reagent for TNF-α detection.

The present disclosure also provides the use of the above peptide with high affinity for TNF-α in the preparation of a TNF-α antagonist.

The present disclosure also provides the use of the above peptide with high affinity for TNF-α in the preparation of an agent for detection of TNF-α expression or a clinical testing agent.

The present disclosure also provides the use of a gene having nucleotide sequence as set forth in SEQ.ID.NO.2 in the preparation of a TNF-α antagonist or in a tracer detection.

The peptide of the present invention having the amino acid sequence of SEQ.ID.NO.1 can be used as a TNF-α antagonist drug. The peptide has a high binding affinity for TNF-α, inhibits the biological activity of TNF-α and prevents the TNF-α induced inflammatory damage. The peptide of the present invention having the amino acid sequence of SEQ.ID.NO.3 can also be used as a potential TNF-α antagonist drug, and the peptide also has a high binding affinity for TNF-α and inhibits the biological activity of TNF-α.

Affinity Assay of the Peptide to TNF-α.

A 96-well ELISA plate was coated with 2 μg/ml TNF-α solution at 4° C. overnight. Different concentrations of peptide 632 labeled with FITC were added to each well and incubated for 2 h. After incubation, HRP-conjugated anti-FITC monoclonal antibody was added, incubated for 1 h, and then ABTS coloring solution was added. After color development for 1 h, the OD value at 410 nm was measured using a microplate reader, and GraphPad Prism 5 was used for plotting and analysis. The results demonstrate that peptide 632 has a strong affinity for TNF-α protein, with a dissociation constant Kd of 138 nM.

Effect of the Peptide on the Inflammation Indexes in an Animal Model of Inflammation.

The experimental animals were divided into three groups: blank group, a non-related peptide control group and an antagonist peptide (peptide 632) group. Using mice as an example, male Kunming mice of 6 weeks old were injected subcutaneously at right abdomen for 3 consecutive days. After the last injection, mice of each group were smeared with p-xylene on both sides of the right auricle. 1 h after the treatment, mice were sacrificed, and the left and right ears of the mice were cut. An ear swelling puncher was used to cut down ears to obtain ear pieces. Swelling degree of mouse ear were obtained by subtracting the weighs of left ear piece from the weighs of right ear piece. Comparing the differences among different groups, it was found that the antagonist peptide can significantly inhibit the swelling of the mouse ear, indicating that the peptide can prevent inflammation-induced damage.

It can be seen that the peptide provided herein has a strong affinity for TNF-α protein and can prevent TNF-α-induced inflammatory damage. Thus, the peptide can be used to inhibit the biological activity of TNF-α, and to treat inflammatory diseases that are strongly associated with TNF-α.

DETAILED DESCRIPTION OF THE EMBODIMENTS

Figure 1:
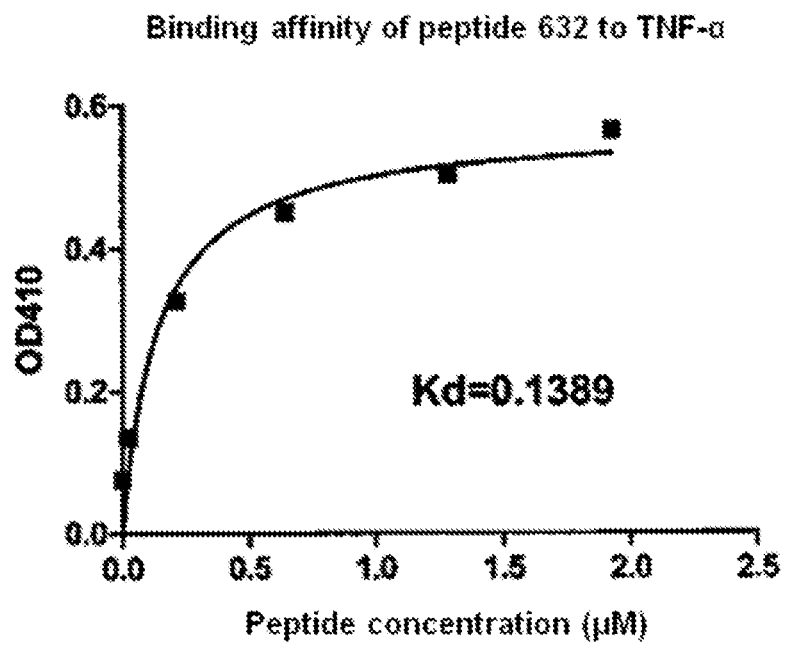
FIG. 1 shows the binding affinity of peptide 632 to TNF-α protein.

1. Acquisition and Modification of Peptide Sequence

Desired peptides having an affinity for TNF-α protein were artificially synthesized by a chemical method.

2. Synthesis and Purification of the Peptide

Lys (Dde)-Wang Resin was soaked in DCM for 10 min, and then DCM was drained. 25% piperidine (piperidine/DMF) with 3-fold volume was added into the resin, and then the piperidine was drained after bubbling with nitrogen for 20 min. DMF was added and blown for 1 min. After 6 cycles, DMF was drained, and the resin was detected to be blue by ninhydrin. The product is H-Lys (Dde)-Wang Resin. Three equivalents of Fmoc-Val-OH, HATU, DIEA in DMF were added to the resin. After blowing for 20 min with nitrogen, the DMF reaction solution was drained. DMF was added and blown for 1 min with nitrogen before draining. After 3 cycles, the resin was detected to be transparent by ninhydrin. The product is Fmoc-Val-Lys (Dde)-Wang Resin. The crude product was obtained by the same method. Purification was carried out on a Hanbang YCM C18 column using acetonitrile and Milli-Q water. In this way, a peptide with high specificity and high activity was obtained.

3. Affinity Assay of Peptide 632 to TNF-α and its Effect on the Inflammation Indexes in Animal Model (1) Experimental Results of the Affinity of Peptide 632 to TNF-α Protein.

A 96-well ELISA plate was coated with 2 μg/ml TNF-α protein at 4° C. overnight. After blocking with BSA, different concentrations of peptide 632 labeled with FITC were added to each well and incubated for 2 h. After incubation, HRP-conjugated anti-FITC monoclonal antibody was added, incubated for 1 h, and then ABTS coloring solution was added. After color development for 1 h, the OD value at 410 nm was measured using a microplate reader, and GraphPad Prism 5 was used for plotting and analysis. The results demonstrate that peptide 632 has a high binding affinity for TNF-α protein, with a dissociation constant Kd of 138 nM.

(2) Effect of Peptide 632 on the Inflammation Indexes in an Animal Model of Inflammation.

The experimental animals were divided into three groups: blank group, a non-related peptide control group and an antagonist peptide (peptide 632) group. Male Kunming mice of 6 weeks old were injected subcutaneously with peptides at right abdomen for 3 consecutive days. 30 min after the last injection, mice of each group were smeared with p-xylene (0.03 ml/per mouse) on both sides of the right auricle to induce inflammation, and the left auricle was served as normal control. 1 h after the inflammation, animals were sacrificed, and the ears of mice were completely cut and marked to distinguish the left and right ears of the same mouse. Both sides of the mouse ear were coated with the same piece of paper. An ear swelling puncher with a diameter of 8 mm was used to cut the same parts of the left and right ears to obtain ear pieces. The ear pieces were weighed together with papers, and the results were recorded. Swelling degree of mouse ear=weighs of the ear piece being induced of inflammation−weighs of the ear piece without inflammation.

Figure 2:
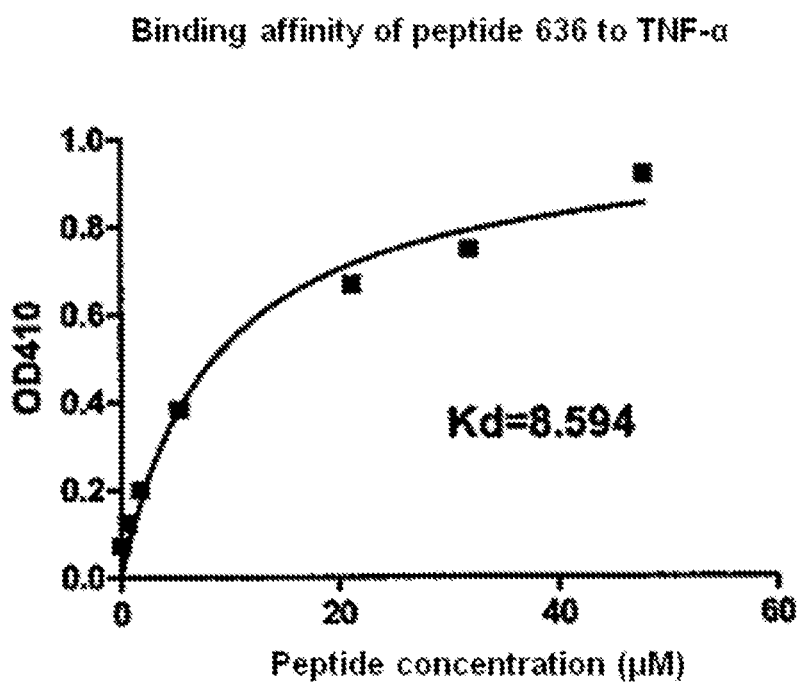
FIG. 2 shows the binding affinity of peptide 636 to TNF-α protein.
Figure 3:
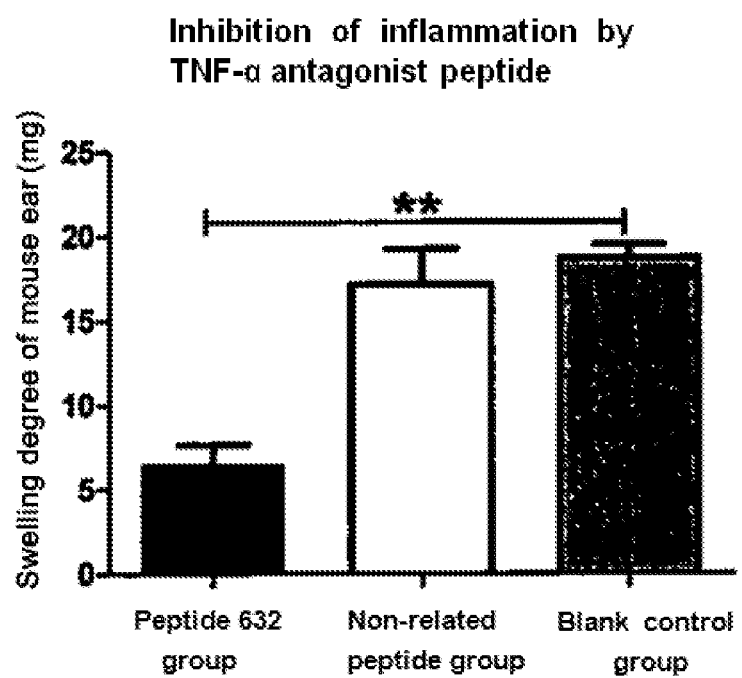
FIG. 3 shows the extent to which peptide 632 inhibits inflammation in Kunming mice model of inflammation.

As shown in FIG. 1 and FIG. 2, peptide 632 has a high binding affinity for TNF-α protein. Animal experiments showed that the ear swelling degree of the experimental group injected with peptide 632 was significantly lower than those of the control group. The above results indicate that peptide 632 can achieve the effect of preventing inflammatory damage by antagonizing the activity of TNF-α.

4. Industrial Applicability

As an important inflammatory factor, TNF-α plays an important role in the occurrence and the development of inflammation. In immune diseases induced by inflammation, the increasing level of TNF-α induces a series of pathogenic reactions and expression of related cytokines, causing tissue damage. Antagonism of TNF-α has proven to be an effective treatment in various inflammatory diseases such as rheumatoid arthritis and psoriasis. However, current antagonists are focused on monoclonal antibodies and their derivatives. Monoclonal antibodies and their derivatives have strong side effects, especially they have high immunogenicity, which limits their use in drug. Therefore, the peptide with high binding affinity for TNF-α provided herein not only has a strong affinity for TNF-α, but also inhibits the biological activity of TNF-α. Thus, the peptide of the present invention can prevent related inflammatory damage and can be used as a potential TNF-α antagonist drug. In addition, the modified peptide 632 can be used as a detection reagent to detect the expression of TNF-α protein.

Sequence lists

SEQ. ID. NO. 1 (N terminal → C terminal):
HYIDFRW

SEQ. ID. NO. 2 (N terminal → C terminal):
CATTATATTGATTTTAGGTGG

SEQ. ID. NO. 3 (N terminal → C terminal):
KASGSPSGFWPS

SEQ. ID. NO. 4 (N terminal → C terminal):
HYIDFRWDMKASGSPSGFWPS

The invention claimed is:

1. A peptide with high affinity for TNF-α, wherein the peptide has an amino acid sequence of SEQ.ID.NO.4.

2. A peptide modified by a biological material or a chemical group, comprising the peptide with high affinity for TNF-α according to claim 1 as a core sequence, and wherein its C-terminus, N-terminus or a side-chain group is modified by PEG or covalently modified by other molecular groups.

3. A modified peptide, comprising the peptide with high affinity for TNF-α according to claim 1, wherein the modified peptide is labeled with a FITC fluorophore, an isotope, a chemiluminescent group or an enzyme reagent for TNF-α detection.

4. A method for detection of TNF-α expression, the method comprising administering a peptide with high affinity for TNF-α according to claim 1 to detect the presence of TNF-α in biological samples.

* * * * *